(12) United States Patent
Peffly et al.

(10) Patent No.: US 9,198,847 B2
(45) Date of Patent: Dec. 1, 2015

(54) PERSONAL CARE COMPOSITION CONTAINING A NON-GUAR GALACTOMANNAN POLYMER DERIVATIVE AND AN ANIONIC SURFACTANT SYSTEM

(75) Inventors: Marjorie Mossman Peffly, Cincinnati, OH (US); James Anthony Staudigel, Cincinnati, OH (US); Salvador Pliego, Montclair, NJ (US); George Endel Deckner, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/264,497

(22) Filed: Nov. 1, 2005

(65) Prior Publication Data

US 2008/0139432 A1 Jun. 12, 2008

Related U.S. Application Data

(60) Provisional application No. 60/625,633, filed on Nov. 5, 2004.

(51) Int. Cl.
*A61K 8/73* (2006.01)
*A61Q 5/02* (2006.01)
*A61K 8/46* (2006.01)
*A61Q 5/12* (2006.01)

(52) U.S. Cl.
CPC ............... *A61K 8/463* (2013.01); *A61K 8/737* (2013.01); *A61Q 5/02* (2013.01); *A61Q 5/12* (2013.01); *A61K 2800/5426* (2013.01)

(58) Field of Classification Search
CPC .................................. A61Q 5/02; A61Q 5/12
USPC ................... 510/122; 424/70, 70.1, 400, 401
See application file for complete search history.

(56) References Cited

U.S. PATENT DOCUMENTS

| | | | |
|---|---|---|---|
| 2,694,668 A | 11/1954 | Fricke | |
| 2,809,971 A | 10/1957 | Bernstein et al. | |
| 2,826,551 A | 3/1958 | Geen | |
| 3,152,046 A | 10/1964 | Kapral | |
| 3,236,733 A | 2/1966 | Karsten et al. | |
| 3,753,196 A | 8/1973 | Kurtz et al. | |
| 3,761,418 A | 9/1973 | Parran, Jr. | |
| 3,964,500 A | 6/1976 | Drakoff | |
| 4,061,602 A | 12/1977 | Oberstar et al. | |
| 4,089,945 A | 5/1978 | Brinkman et al. | |
| 4,323,683 A | 4/1982 | Bolich, Jr. et al. | |
| 4,345,080 A | 8/1982 | Bolich, Jr. | |
| 4,364,837 A | 12/1982 | Pader | |
| 4,379,753 A | 4/1983 | Bolich, Jr. | |
| 4,470,982 A | 9/1984 | Winkler | |
| 4,741,855 A | 5/1988 | Grote et al. | |
| 4,753,659 A * | 6/1988 | Bayerlein et al. | 8/561 |
| 4,885,107 A | 12/1989 | Wetzel | |
| 5,011,681 A * | 4/1991 | Ciotti et al. | 510/136 |
| 5,104,646 A | 4/1992 | Bolich, Jr. et al. | |
| 5,106,609 A | 4/1992 | Bolich, Jr. et al. | |
| RE34,584 E | 4/1994 | Grote et al. | |
| 5,378,830 A * | 1/1995 | Yeh | 536/118 |
| 5,540,853 A * | 7/1996 | Trinh et al. | 510/101 |
| 5,552,462 A * | 9/1996 | Yeh | 524/55 |
| 5,756,436 A * | 5/1998 | Royce et al. | 510/122 |
| 5,756,720 A * | 5/1998 | Chowdhary | 536/124 |
| 6,281,172 B1 * | 8/2001 | Warren et al. | 507/110 |
| 6,338,855 B1 | 1/2002 | Albacarys et al. | |
| 6,589,517 B1 * | 7/2003 | McKelvey et al. | 424/70.1 |
| 6,930,078 B2 * | 8/2005 | Wells et al. | 510/121 |
| 7,262,157 B2 * | 8/2007 | Utz et al. | 510/121 |
| 2002/0119174 A1 * | 8/2002 | Gardlik et al. | 424/401 |
| 2003/0133899 A1 | 7/2003 | Fan et al. | |
| 2003/0223951 A1 | 12/2003 | Geary et al. | |

(Continued)

FOREIGN PATENT DOCUMENTS

| | | |
|---|---|---|
| GB | 849433 | 9/1960 |
| JP | 10-036403 A | 2/1998 |
| JP | 2000-103724 | 4/2000 |
| JP | 2003-327603 A | 11/2003 |
| WO | WO-2005/073255 | 8/2005 |

OTHER PUBLICATIONS

International Search Report, PCT/US2005/039600, dated Mar. 23, 2006 (6 pages).

(Continued)

*Primary Examiner* — Nicole M Buie-Hatcher
*Assistant Examiner* — M. Reza Asdjodi
(74) *Attorney, Agent, or Firm* — James T. Fondriest; Angela K. Haughey

(57) ABSTRACT

Personal care compositions comprise (a) from about 0.01 wt. % to about 10 wt. % of a galactomannan polymer derivative having a mannose to galactose ratio of greater than 2:1 on a monomer to monomer basis, the galactomannan polymer derivative selected from a cationic galactomannan polymer derivative and an amphoteric galactomannan polymer derivative having a net positive charge, wherein the cationic galactomannan polymer has a molecular weight from about 1,000 to about 10,000,000 and a cationic charge density from about 0.7 meq/g to about 7 meq/g; (b) from about 5 wt. % to about 35 wt. % of an anionic surfactant system, the anionic surfactant system comprising at least one anionic surfactant and having an ethoxylate level and an anion level, (i) wherein the ethoxylate level is from about 1 to about 6, and (ii) wherein the anion level is from about 1.5 to about 6; and (c) an aqueous carrier. Personal care compositions as described above further comprise from about 0.01 wt. % to about 10 wt. % of one or more conditioning agents. Methods of treating hair or skin comprise applying the personal care compositions as described above to the hair or skin and rinsing the hair or skin.

12 Claims, No Drawings

(56) References Cited

U.S. PATENT DOCUMENTS

| | | |
|---|---|---|
| 2004/0234483 A1 | 11/2004 | Peffly et al. |
| 2004/0234484 A1 | 11/2004 | Peffley et al. |
| 2005/0026794 A1* | 2/2005 | Utz et al. .................... 510/130 |
| 2005/0075497 A1* | 4/2005 | Utz et al. .................... 536/114 |
| 2005/0202984 A1* | 9/2005 | Schwartz et al. ............ 510/119 |
| 2006/0099167 A1* | 5/2006 | Staudigel et al. .......... 424/70.13 |
| 2007/0027051 A1 | 2/2007 | Staudigel et al. |

OTHER PUBLICATIONS

Encyclopedia of Polymer Science and Engineering, vol. 15, 2d ed., pp. 204-308, John Wiley & Sons, Inc. (1989).

* cited by examiner

PERSONAL CARE COMPOSITION CONTAINING A NON-GUAR GALACTOMANNAN POLYMER DERIVATIVE AND AN ANIONIC SURFACTANT SYSTEM

CROSS REFERENCE TO RELATED APPLICATIONS

This application claims the benefit of U.S. Provisional application Ser. No. 60/625,633, filed on Nov. 5, 2004.

FIELD OF THE INVENTION

The present invention relates to personal care compositions comprising a galactomannan polymer derivative having a mannose to galactose ratio of greater than 2:1. More particularly, the present invention relates to personal care compositions comprising a particular anionic surfactant system and a cationic or amphoteric galactomannan polymer derivative having a mannose to galactose ratio of greater than 2:1. In one aspect, the present invention relates to personal care compositions as described above which further comprise one or more conditioning agents.

BACKGROUND OF THE INVENTION

Personal care compositions comprising various combinations of detersive surfactants and conditioning agents are known. These products typically comprise an anionic detersive surfactant in combination with a conditioning agent such as silicone, hydrocarbon oil, fatty esters, or combinations thereof. These products have become more popular among consumers as a means of conveniently obtaining hair or skin conditioning and cleansing performance all from a single personal care product.

Many personal care compositions, though, do not provide sufficient deposition of conditioning agents onto hair and skin during the cleansing process. Without such deposition, large proportions of conditioning agent are rinsed away during the cleansing process, and, therefore, provide little or no conditioning benefit. Without sufficient deposition of the conditioning agent on the hair and skin, relatively high levels of conditioning agents may be needed in the personal care composition to provide adequate conditioning performance. However, high levels of a conditioning agent can increase raw material costs, reduce lathering, and present product stability concerns.

Obtaining good deposition of a conditioning agent is further complicated by the action of detersive surfactants in the personal care composition. Detersive surfactants are designed to carry away or remove oil, grease, dirt, and particulate matter from the hair and skin. As a result, the detersive surfactants can interfere with deposition of the conditioning agent and can remove both deposited and non-deposited conditioning agent during rinsing. Consequently, after rinsing, the deposition of the conditioning agent onto the hair and skin is reduced, which, in turn, reduces conditioning performance. Therefore, to achieve desired conditioning performance with a given conditioning agent, a specific anionic surfactant system may be needed for use in combination with the given conditioning agent.

One method for improving deposition of a conditioning agent involves the use of certain cationic deposition polymers. Commonly used cationic deposition polymers include natural polymers, such as guar gum polymers that have been modified with cationic substituents. Guar gum polymers are galactomannans containing two mannose monomers with a glycoside linkage and one galactose monomer attached to a hydroxyl group of the mannose monomers (i.e., guar gum polymers have a mannose to galactose ratio of 2:1 on a monomer to monomer basis). Selecting a cationic guar deposition polymer with sufficient charge density and molecular weight, in combination with an optimized surfactant system, results in sufficient deposition of conditioning agents. However, to achieve this sufficient deposition of conditioning agents in shampoo or body wash compositions using a cationic guar polymer, a relatively high level of such cationic guar polymer generally must be deposited on the hair or skin. Moreover, the cost of such cationic guar polymer is relatively high. As a result, incorporation of cationic guar polymer can add to the manufacturing costs of such personal cleansing compositions.

Accordingly, there is a continuing need for a personal cleansing composition which delivers superior conditioning benefits to hair and/or skin, without a reduced cleansing performance, through relatively low deposition of an inexpensive cationic or amphoteric polymer in combination with a particular anionic surfactant system.

SUMMARY OF THE INVENTION

The present invention is directed to a personal care composition comprising:
a) from about 0.01 wt. % to about 10 wt. % of a galactomannan polymer derivative having a mannose to galactose ratio of greater than 2:1 on a monomer to monomer basis, said galactomannan polymer derivative selected from the group consisting of a cationic galactomannan polymer derivative and an amphoteric galactomannan polymer derivative having a net positive charge;
  i) wherein said galactomannan polymer derivative has a molecular weight from about 1,000 to about 10,000,000; and
  ii) wherein said galactomannan polymer derivative has a cationic charge density from about 0.7 meq/g to about 7 meq/g;
b) from about 5 wt. % to about 35 wt. % of an anionic surfactant system, said anionic surfactant system comprising at least one anionic surfactant and having an ethoxylate level and an anion level,
  i) wherein said ethoxylate level is from about 1 to about 6; and
  ii) wherein said anion level is from about 1.5 to about 6; and
c) an aqueous carrier.

Additionally, the present invention is directed to a personal care composition as described above further comprising from about 0.01 wt. % to about 10 wt. % of one or more conditioning agents.

The present invention is also directed to a method of treating hair or skin comprising the steps of applying the personal care composition as described above to the hair or skin and rinsing the hair or skin.

DETAILED DESCRIPTION OF THE INVENTION

While the specification concludes with claims that particularly point out and distinctly claim the invention, it is believed the present invention will be better understood from the following description.

The personal care compositions of the present invention comprise a cationic galactomannan polymer, an anionic surfactant system, and an aqueous carrier. Each of these essential components, as well as preferred or optional components, is described in detail hereinafter.

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein.

All molecular weights as used herein are weight average molecular weights expressed as grams/mole, unless otherwise specified.

The term "charge density", as used herein, refers to the ratio of the number of net positive charges on a monomeric unit of which a polymer is comprised to the molecular weight of said monomeric unit. The charge density multiplied by the polymer molecular weight determines the number of positively charged sites on a given polymer chain.

The term "polymer" as used herein shall include materials whether made by polymerization of one type of monomer or made by two (i.e., copolymers) or more types of monomers.

The term "water-soluble" as used herein, means that the polymer is soluble in water in the present composition. In general, the polymer should be soluble at 25° C. at a concentration of at least 0.1% by weight of the water solvent, preferably at least 1%, more preferably at least 5%, most preferably at least 15%.

The term "water-insoluble" as used herein, means that a compound is not soluble in water in the present composition. Thus, the compound is not miscible with water.

The term "particle size" as used herein refers to the average mean particle size of a group of particles in the final composition of the present invention. For opaque compositions and/or those containing small to large sized particles (i.e., about 100 nm to about 50 μm), particle size may be measured by means of a laser light scattering technique, using a Horiba model LA 910 Laser Scattering Particle Size Distribution Analyzer (Horiba Instruments, Inc. Irvine, Calif., USA). For substantially clear compositions and/or those containing nano sized particles (i.e., less than about 100 nm), particle size may be measured by means of a dynamic light scattering controlled reference method (i.e., which uses a heterodyne detection technique), using a Microtrac® model UPA 150 Ultrafine Particle Size Analyzer (Honeywell, Inc., Industrial Automation and Control, St. Petersburg, Fla., USA).

The transparency of the composition is measured by Ultra-Violet/Visible (UV/VIS) spectrophotometry, which determines the absorption or transmission of UV/VIS light by a sample. A light wavelength of 600 nm has been shown to be adequate for characterizing the degree of clarity of non-colored cosmetic compositions.

A. Galactomannan Polymer Derivative

The personal care compositions of the present invention comprise galactomannan polymer derivatives having a mannose to galactose ratio of greater than 2:1 on a monomer to monomer basis, the galactomannan polymer derivative selected from the group consisting of a cationic galactomannan polymer derivative and an amphoteric galactomannan polymer derivative having a net positive charge. As used herein, the term "cationic galactomannan" refers to a galactomannan polymer to which a cationic group is added. The term "amphoteric galactomannan" refers to a galactomannan polymer to which a cationic group and an anionic group are added such that the polymer has a net positive charge.

Galactomannan polymers are present in the endosperm of seeds of the Leguminosae family. Galactomannan polymers are made up of a combination of mannose monomers and galactose monomers. The galactomannan molecule is a straight chain mannan branched at regular intervals with single membered galactose units on specific mannose units. The mannose units are linked to each other by means of β (1-4) glycosidic linkages. The galactose branching arises by way of an α (1-6) linkage. The ratio of mannose monomers to galactose monomers varies according to the species of the plant and also is affected by climate. Guar is an example of one type of a galactomannan polymer, specifically having a mannose to galactose ratio of 2 monomers of mannose to 1 monomer of galactose. Galactomannan polymers of the present invention have a ratio of mannose to galactose of greater than 2:1 on a monomer to monomer basis (i.e., non-guar galactomannan polymers). Preferably, the ratio of mannose to galactose is greater than about 3:1, and more preferably the ratio of mannose to galactose is greater than about 4:1. Analysis of mannose to galactose ratios is well known in the art and is typically based on the measurement of the galactose content.

The gum for use in preparing the non-guar galactomannan polymer derivatives is typically obtained as naturally occurring material such as seeds or beans from plants. Examples of various non-guar galactomannan polymers include but are not limited to Tara gum (3 parts mannose/1 part galactose), Locust bean or Carob (4 parts mannose/1 part galactose), and Cassia gum (5 parts mannose/1 part galactose).

The cationic galactomannan polymer derivatives for use in the personal care compositions of the present invention have a molecular weight from about 1,000 to about 10,000,000. In one embodiment of the present invention, the cationic galactomannan polymer derivatives have a molecular weight from about 5,000 to about 3,000,000. As used herein, the term "molecular weight" refers to the weight average molecular weight. The weight average molecular weight may be measured by gel permeation chromatography.

The personal care compositions of the present invention include galactomannan polymer derivatives which have a cationic charge density from about 0.7 meq/g to about 7 meq/g. In one embodiment of the present invention, the galactomannan polymer derivatives have a charge density from about 0.9 meq/g to about 7 meq/g. The degree of substitution of the cationic groups onto the galactomannan structure should be sufficient to provide the requisite cationic charge density.

In one embodiment of the present invention, the galactomannan polymer derivative is a cationic derivative of the non-guar galactomannan polymer, which is obtained by reaction between the hydroxyl groups of the galactomannan polymer and reactive quaternary ammonium compounds. Suitable quaternary ammonium compounds for use in forming the cationic galactomannan polymer derivatives include those conforming to the general formula:

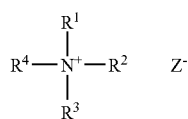

wherein where $R^1$, $R^2$ and $R^3$ are methyl or ethyl groups; $R^4$ is either an epoxyalkyl group of the general formula:

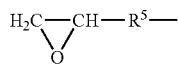

or $R^4$ is a halohydrin group of the general formula:

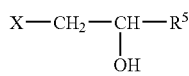

wherein $R^5$ is a $C_1$ to $C_3$ alkylene; X is chlorine or bromine, and Z is an anion such as $Cl^-$, $Br^-$, $I^-$ or $HSO_4^-$.

Cationic non-guar galactomannan polymer derivatives formed from the reagents described above are represented by the general formula:

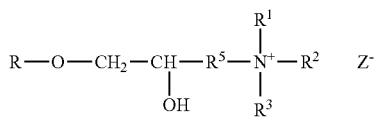

wherein R is the gum. Preferably, the cationic galactomannan derivative is a gum hydroxypropyltrimethylammonium chloride, which can be more specifically represented by the general formula:

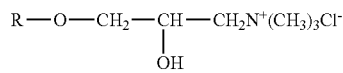

In another embodiment of the present invention, the galactomannan polymer derivative is an amphoteric galactomannan polymer derivative having a net positive charge, obtained when the cationic galactomannan polymer derivative further comprises an anionic group.

The personal care compositions of the present invention comprise galactomannan polymer derivatives at a range of about 0.01% to about 10%, and more preferably from about 0.05% to about 5%, by weight of the composition.

B. Anionic Surfactant System—Ethoxylate Level and Anion Level

The personal care compositions of the present invention comprise an anionic surfactant system. The anionic surfactant system is included to provide cleaning performance to the composition. The anionic surfactant system comprises at least one anionic surfactant, and optionally an amphoteric surfactant, a zwitterionic surfactant, a cationic surfactant, a nonionic surfactant, or a combination thereof. Such surfactants should be physically and chemically compatible with the essential components described herein, or should not otherwise unduly impair product stability, aesthetics, or performance.

Suitable anionic surfactant components for use in the personal care composition herein include those that are known for use in hair care or other personal care compositions. The concentration of the anionic surfactant system in the personal care composition should be sufficient to provide the desired cleaning and lather performance, and generally ranges from about 5% to about 35%, preferably from about 8% to about 30%, more preferably from about 10% to about 25%, by weight of the composition.

In considering the performance characteristics of a personal care composition, such as wet conditioning performance, dry conditioning performance, and conditioning ingredient deposition on hair, it is necessary to optimize the levels and types of surfactant in order to maximize the performance potential of polymer systems. The anionic surfactant system for use in the personal care compositions of the present invention has an ethoxylate level and an anion level, wherein the ethoxylate level is from about 1 to about 6, and wherein the anion level is from about 1.5 to about 6, both as calculated below.

An optimal ethoxylate level can be calculated based on the stoichiometry of the surfactant structure, which in turn is based on a particular molecular weight of the surfactant where the number of moles of ethoxylation is known. Likewise, given a specific molecular weight of a surfactant and an anionization reaction completion measurement, the anion level can be calculated. Analytical techniques have been developed to measure ethoxylation or anionization within surfactant systems. The Level of Ethoxylate and the Level of Anion (both molar levels) representative of a particular surfactant system are calculated from the percent ethoxylation and percent anion of individual surfactants in the following manner:

Level of Ethoxylate in a composition=percent ethoxylation multiplied by percent active ethoxylated surfactant (based upon the total weight of the composition).

Level of Anion in a composition=percent anion in ethoxylated surfactant multiplied by percent active ethoxylated surfactant (based upon the total weight of the composition) plus percent anion in non-ethoxylated surfactant multiplied by percent active non-ethoxylated surfactant (based upon the total weight of the composition).

If a composition comprises two or more surfactants having different respective anions (e.g., surfactant A has a sulfate group and surfactant B has a sulfonate group), the Level of Anion in the composition is the sum of the molar levels of each respective anion as calculated above.

Sample Calculation:

Example 1 shows an ethoxylated surfactant that contains 0.294321% ethoxylate and 0.188307% sulfate as the anion and a non-ethoxylated surfactant that contains 0.266845% sulfate as an anion. Both surfactants are 29% active.

Level of Ethoxylate in Example 1=0.294321 multiplied by 7 (% active ethoxylated surfactant). Thus, the Level of Ethoxylate in the composition of Example 1 is approximately 2.06.

Level of Anion in Example 1=0.188307 multiplied by 7 (% active ethoxylated surfactant) plus 0.266845 multiplied by 7 (% active non-ethoxylated surfactant). Thus, the Level of Anion in the composition of Example 1 is approximately 3.19.

The anionic surfactant system comprises at least one anionic surfactant comprising an anion selected from the group consisting of sulfates, sulfonates, sulfosuccinates, isethionates, carboxylates, phosphates, and phosphonates. Preferably, the anion is a sulfate.

Preferred anionic surfactants suitable for use in the personal care compositions are alkyl sulfates and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from about 1 to about 10, and M is a cation such as ammonium, an alkanolamine such as triethanolamine, a monovalent metal such as sodium and potassium, or a polyvalent metal cation such as magnesium and calcium. Solubility of the surfactant will depend upon the particular anionic surfactants and cations chosen.

Preferably, R has from about 8 to about 18 carbon atoms, more preferably from about 10 to about 16 carbon atoms, even more preferably from about 12 to about 14 carbon atoms, in both the alkyl sulfates and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with from about 0 to about 10, preferably from about 2 to about 5, more preferably about 3, molar proportions of ethylene oxide, and the resulting mixture of molecular species having, for example, an average of 3 moles of ethylene oxide per mole of alcohol is sulfated and neutralized.

Specific non-limiting examples of alkyl ether sulfates which may be used in the personal care compositions of the present invention include sodium and ammonium salts of coconut alkyl triethylene glycol ether sulfate, tallow alkyl triethylene glycol ether sulfate, and tallow alkyl hexa-oxyethylene sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide. Such a mixture also comprises from about 0% to about 20% by weight $C_{12-13}$ compounds; from about 60% to about 100% by weight of $C_{14-15-16}$ compounds; from about 0% to about 20% by weight of $C_{17-18-19}$ compounds; from about 3% to about 30% by weight of compounds having a degree of ethoxylation of 0; from about 45% to about 90% by weight of compounds having a degree of ethoxylation from about 1 to about 4; from about 10% to about 25% by weight of compounds having a degree of ethoxylation from about 4 to about 8; and from about 0.1% to about 15% by weight of compounds having a degree of ethoxylation greater than about 8.

Another suitable class of anionic surfactants are the water-soluble salts of the organic, sulfuric acid reaction products of the general formula $R_1$—$SO_3$-M wherein $R_1$ is chosen from the group consisting of a straight or branched chain, saturated aliphatic hydro-carbon radical having from 8 to 24, preferably 12 to 18, carbon atoms; and M is a cation. Important examples are the salts of an organic sulfuric acid reaction product of a hydrocarbon of the methane series, including iso-, neo-, ineso-, and n-paraffins, having 8 to 24 carbon atoms, preferably 12 to 18 carbon atoms, and a sulfonating agent e.g., $SO_3$, $H_2SO_4$, oleum, obtained according to known sulfonation methods, including bleaching and hydrolysis. Preferred are alkali metal and ammonium sulfonated $C_{12-18}$-n-paraffins.

Preferred anionic surfactants for use in the personal care compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, and combinations thereof.

Still other suitable anionic surfactants are the reaction products of fatty acids esterified with isethionic acid and neutralized with sodium hydroxide where, for example, the fatty acids are derived from coconut oil or palm kernel oil, and sodium or potassium salts of fatty acid amides of methyl tauride where, for example, the fatty acids are derived from coconut oil or palm kernel oil.

Other anionic surfactants suitable for use in the shampoo compositions are the succinnates, examples of which include disodium N-octadecylsulfosuccinnate, disodium lauryl sulfosuccinate, diammonium lauryl sulfosuccinate, tetrasodium N-(1,2-dicarboxyethyl)-N-octadecylsulfosuccinnate, diamyl ester of sodium sulfosuccinic acid, dihexyl ester of sodium sulfosuccinic acid, and dioctyl esters of sodium sulfosuccinic acid.

Other suitable anionic surfactants include olefin sulfonates having about 10 to about 24 carbon atoms. In this context, the term "olefin sulfonates" refers to compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The alpha-olefins from which the olefin sulfonates are derived are mono-olefins having from about 10 to about 24 carbon atoms, preferably from about 12 to about 16 carbon atoms. Preferably, they are straight chain olefins.

Another class of anionic surfactants suitable for use herein is the beta-alkyloxy alkane sulfonates. These surfactants conform to the formula:

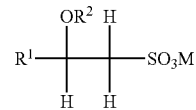

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described.

In addition to the sulfates, isethionates, sulfonates, sulfosuccinates described above, other potential anions for the anionic surfactant include phosphonates, phosphates, and carboxylates.

The personal care compositions of the present invention may also include one or more additional surfactants selected from the group consisting of amphoteric surfactants, zwitterionic surfactants, cationic surfactants, and nonionic surfactants. Suitable amphoteric, zwitterionic, cationic surfactants, or nonionic surfactants for use in the personal care compositions herein include those which are known for use in hair care or other personal care compositions. Concentration of such surfactants preferably ranges from about 0.5% to about 20%, preferably from about 1% to about 10%, by weight of the composition. Non-limiting examples of suitable surfactants are described in U.S. Pat. Nos. 5,104,646 and 5,106,609, both to Bolich, Jr. et al.

Non-limiting examples of other surfactants suitable for use in the personal care compositions are described in McCutcheon's, Emulsifiers and Detergents, 1989 Annual, published by M. C. Publishing Co.

C. Aqueous Carrier

The personal care compositions of the present invention comprise an aqueous carrier. The level and species of the carrier are selected according to the compatibility with other components and other desired characteristic of the product. Generally, the aqueous carrier is present in an amount from about 20% to about 95% by weight of the composition. An aqueous carrier may be selected such that the composition of the present invention may be in the form of, for example, a pourable liquid, a gel, a paste, a dried powder, or a dried film.

Aqueous carriers useful in the present invention include water and water solutions of lower alkyl alcohols. Lower alkyl alcohols useful herein are monohydric alcohols having 1 to 6 carbons, more preferably ethanol and isopropanol.

The pH of the present composition, measured neat, is preferably from about 3 to about 9, more preferably from about 4 to about 8. Buffers and other pH-adjusting agents can be included to achieve the desirable pH.

D. Additional Components

The personal care compositions of the present invention may further comprise one or more additional components known for use in hair care or personal care products, provided that the additional components are physically and chemically compatible with the essential components described herein, or do not otherwise unduly impair product stability, aesthetics or performance. Individual concentrations of such additional components may range from about 0.001% to about 10% by weight of the personal care compositions.

Non-limiting examples of additional components for use in the composition include conditioning agents (e.g., silicones, hydrocarbon oils, fatty esters), particles, anti-dandruff agents, suspending agents, paraffinic hydrocarbons, propellants, viscosity modifiers, dyes, non-volatile solvents or diluents (water-soluble and water-insoluble), pearlescent aids, foam boosters, additional surfactants or nonionic cosurfactants, pediculocides, pH adjusting agents, perfumes, preservatives, chelants, proteins, skin active agents, sunscreens, UV absorbers, and vitamins.

1. Conditioning Agent

In one embodiment of the present invention, the personal care compositions comprise one or more conditioning agents. Conditioning agents include materials which are used to give a particular conditioning benefit to hair and/or skin. The conditioning agents useful in the compositions of the present invention typically comprise a water-insoluble, water-dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix.

One or more conditioning agents are present from about 0.01% to about 10%, preferably from about 0.1% to about 8%, more preferably from about 0.2% to about 4%, by weight of the composition.

In a preferred embodiment of the compositions of the present invention, the weight ratio of conditioning agent to galactomannan polymer derivative is at least about 2:1.

a. Silicone Conditioning Agent

The conditioning agents of the compositions of the present invention may be a water-insoluble silicone conditioning agent. The silicone conditioning agent may comprise volatile silicone, non-volatile silicone, or combinations thereof. The silicone conditioning agent particles may comprise a silicone fluid conditioning agent and may also comprise other ingredients, such as a silicone resin to improve silicone fluid deposition efficiency or enhance glossiness of the hair.

Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the compositions of the present invention preferably have a viscosity, as measured at 25° C., from about 20 to about 2,000,000 centistokes ("csk"), more preferably from about 1,000 to about 1,800,000 csk, even more preferably from about 10,000 to about 1,500,000 csk, more preferably from about 20,000 to about 1,000,000 csk.

In an opaque composition embodiment of the present invention, the personal care composition comprises a non-volatile silicone oil having a particle size as measured in the personal care composition from about 1 μm to about 50 μm. In an embodiment of the present invention for small particle application to the hair, the personal care composition comprises a non-volatile silicone oil having a particle size as measured in the personal care composition from about 100 nm to about 1 μm. A substantially clear composition embodiment of the present invention comprises a non-volatile silicone oil having a particle size as measured in the personal care composition of less than about 100 nm.

Non-volatile silicone oils suitable for use in compositions of the present invention may be selected from organo-modified silicones and fluoro-modified silicones. In one embodiment of the present invention, the non-volatile silicone oil is an organo-modified silicone which comprises an organo group selected from the group consisting of alkyl groups, alkenyl groups, hydroxyl groups, amine groups, quaternary groups, carboxyl groups, fatty acid groups, ether groups, ester groups, mercapto groups, sulfate groups, sulfonate groups, phosphate groups, propylene oxide groups, and ethylene oxide groups. In a particular embodiment of the present invention, the non-volatile silicone oil is dimethicone.

Background material on silicones including sections discussing silicone fluids, gums, and resins, as well as manufacture of silicones, are found in *Encyclopedia of Polymer Science and Engineering*, vol. 15, 2d ed., pp 204-308, John Wiley & Sons, Inc. (1989).

Silicone fluids suitable for use in the compositions of the present invention are disclosed in U.S. Pat. No. 2,826,551, U.S. Pat. No. 3,964,500, U.S. Pat. No. 4,364,837, British Pat. No. 849,433, and *Silicon Compounds*, Petrarch Systems, Inc. (1984).

b. Organic Conditioning Oils

The conditioning agent of the compositions of the present invention may also comprise at least one organic conditioning oil, either alone or in combination with other conditioning agents, such as the silicones described above.

i. Hydrocarbon Oils

Suitable organic conditioning oils for use as conditioning agents in the compositions of the present invention include, but are not limited to, hydrocarbon oils having at least about 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils preferably are from about $C_{12}$ to about $C_{19}$. Branched chain hydrocarbon oils, including hydrocarbon polymers, typically will contain more than 19 carbon atoms.

ii. Polyolefins

Organic conditioning oils for use in the compositions of the present invention can also include liquid polyolefins, more preferably liquid poly-α-olefins, more preferably hydrogenated liquid poly-α-olefins. Polyolefins for use herein are prepared by polymerization of $C_4$ to about $C_{14}$ olefenic monomers, preferably from about $C_6$ to about $C_{12}$.

iii. Fatty Esters

Other suitable organic conditioning oils for use as the conditioning agent in the compositions of the present invention include fatty esters having at least 10 carbon atoms. These fatty esters include esters with hydrocarbyl chains derived from fatty acids or alcohols. The hydrocarbyl radicals of the fatty esters hereof may include or have covalently bonded thereto other compatible functionalities, such as amides and alkoxy moieties (e.g., ethoxy or ether linkages, etc.).

iv. Fluorinated Conditioning Compounds

Fluorinated compounds suitable for delivering conditioning to hair or skin as organic conditioning oils include perfluoropolyethers, perfluorinated olefins, fluorine based specialty polymers that may be in a fluid or elastomer form similar to the silicone fluids previously described, and perfluorinated dimethicones.

v. Fatty Alcohols

Other suitable organic conditioning oils for use in the personal care compositions of the present invention include, but are not limited to, fatty alcohols having at least about 10 carbon atoms, more preferably about 10 to about 22 carbon atoms, most preferably about 12 to about 16 carbon atoms.

vi. Alkyl Glucosides and Alkyl Glucoside Derivatives

Suitable organic conditioning oils for use in the personal care compositions of the present invention include, but are not limited to, alkyl glucosides and alkyl glucoside derivatives. Specific non-limiting examples of suitable alkyl glucosides and alkyl glucoside derivatives include Glucam E-10, Glucam E-20, Glucam P-10, and Glucquat 125 commercially available from Amerchol.

c. Other Conditioning Agents i. Quaternary Ammonium Compounds

Suitable quaternary ammonium compounds for use as conditioning agents in the personal care compositions of the present invention include, but are not limited to, hydrophilic quaternary ammonium compounds with a long chain substituent having a carbonyl moiety, like an amide moiety, or a phosphate ester moiety or a similar hydrophilic moiety.

Examples of useful hydrophilic quaternary ammonium compounds include, but are not limited to, compounds designated in the CTFA Cosmetic Dictionary as ricinoleamidopropyl trimonium chloride, ricinoleamido trimonium ethylsulfate, hydroxy stearamidopropyl trimoniummethylsulfate and hydroxy stearamidopropyl trimonium chloride, or combinations thereof.

ii. Polyethylene Glycols

Additional compounds useful herein as conditioning agents include polyethylene glycols and polypropylene glycols having a molecular weight of up to about 2,000,000 such as those with CTFA names PEG-200, PEG-400, PEG-600, PEG-1000, PEG-2M, PEG-7M, PEG-14M, PEG-45M and mixtures thereof.

2. Natural Cationic Deposition Polymers

The personal care compositions of the present invention may also include natural cationic deposition polymers. Generally, such natural cationic deposition polymers may be present at a concentration from about 0.05% to about 5%, by weight of the composition. Suitable natural cationic deposition polymers have a molecular weight of greater than about 5,000. Additionally, such natural deposition polymers have a charge density from about 0.5 meq/g to about 4.0 meq/g at the pH of intended use of the personal care composition, which pH will generally range from about pH 3 to about pH 9, preferably between about pH 4 and about pH 8. The pH of the compositions of the present invention are measured neat.

Suitable natural cationic polymers include those which conform to the following formula:

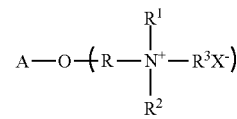

wherein A is an anhydroglucose residual group, such as a cellulose anhydroglucose residual; R is an alkylene oxyalkylene, polyoxyalkylene, or hydroxyalkylene group, or combination thereof; $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less; and X is an anionic counterion. Non-limiting examples of such counterions include halides (e.g., chlorine, fluorine, bromine, iodine), sulfate and methylsulfate. The degree of cationic substitution in these polysaccharide polymers is typically from about 0.01 to about 1 cationic groups per anhydroglucose unit.

In one embodiment of the invention, natural cationic polymers are salts of hydroxyethyl cellulose reacted with trimethyl ammonium substituted epoxide, referred to in the industry (CTFA) as Polyquaternium 10 and available from Amerchol Corp. (Edison, N.J., USA).

Suitable natural cationic polymers also include cationic hydrolyzed starch polymers, such as polymers selected from degraded cationic maize starch, cationic tapioca, cationic potato starch, and mixtures thereof.

3. Synthetic Cationic Deposition Polymers

The personal care compositions of the present invention may also include synthetic cationic deposition polymers. Generally, such synthetic cationic deposition polymers may be present at a concentration from about 0.025% to about 5%, by weight of the composition. Such synthetic cationic deposition polymers have a molecular weight from about 1,000 to about 5,000,000. Additionally, such synthetic cationic deposition polymers have a charge density from about 0.5 meq/g to about 10 meq/g.

Suitable synthetic cationic deposition polymers include those which are water-soluble or dispersible, cationic, non-crosslinked, conditioning copolymers comprising: (i) one or more cationic monomer units; and (ii) one or more nonionic monomer units or monomer units bearing a terminal negative charge; wherein said copolymer has a net positive charge, a cationic charge density of from about 0.5 meq/g to about 10 meq/g, and an average molecular weight from about 1,000 to about 5,000,000.

Non-limiting examples of suitable synthetic cationic deposition polymers are described in United States Patent Application Publication US 2003/0223951 A1 to Geary et al.

4. Anti-Dandruff Actives

The compositions of the present invention may also contain an anti-dandruff active. Suitable non-limiting examples of anti-dandruff actives include pyridinethione salts, azoles, selenium sulfide, particulate sulfur, keratolytic agents, and mixtures thereof. Such anti-dandruff actives should be physically and chemically compatible with the essential components of the composition, and should not otherwise unduly impair product stability, aesthetics or performance.

Pyridinethione anti-microbial and anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

Azole anti-microbials include imidazoles such as climbazole and ketoconazole.

Selenium sulfide compounds are described, for example, in U.S. Pat. No. 2,694,668; U.S. Pat. No. 3,152,046; U.S. Pat. No. 4,089,945; and U.S. Pat. No. 4,885,107.

Sulfur may also be used as a particulate anti-microbial/anti-dandruff agent in the anti-microbial compositions of the present invention.

The present invention may further comprise one or more keratolytic agents such as Salicylic Acid.

Additional anti-microbial actives of the present invention may include extracts of melaleuca (tea tree) and charcoal.

When present in the composition, the anti-dandruff active is included in an amount from about 0.01% to about 5%, preferably from about 0.1% to about 3%, and more preferably from about 0.3% to about 2%, by weight of the composition.

5. Particles

The compositions of the present invention optionally may comprise particles. Particles useful in the present invention can be inorganic, synthetic, or semi-synthetic. In the compositions of the present invention, it is preferable to incorporate no more than about 20%, more preferably no more than about 10% and even more preferably no more than 2%, by weight of the composition, of dispersed water-insoluble particles. In an embodiment of the present invention, the particles have an average mean particle size of less than about 300 µm.

Non-limiting examples of inorganic particles include colloidal silicas, fumed silicas, precipitated silicas, silica gels, magnesium silicate, glass particles, talcs, micas, sericites, and various natural and synthetic clays including bentonites, hectorites, and montmorillonites.

Examples of synthetic particles include silicone resins, poly(meth)acrylates, polyethylene, polyester, polypropylene, polystyrene, polyurethane, polyamide (e.g., Nylon®), epoxy resins, urea resins, acrylic powders, and the like.

Non-limiting examples of hybrid particles include sericite & crosslinked polystyrene hybrid powder, and mica and silica hybrid powder.

6. Opacifying Agents

The compositions of the present invention may also contain one or more opacifying agents. Opacifying agents are typically used in cleansing compositions to impart desired aesthetic benefits to the composition, such as color or pearlescence. In the compositions of the present invention, it is preferable to incorporate no more than about 20%, more preferably no more than about 10% and even more preferably no more than 2%, by weight of the composition, of opacifying agents.

Suitable opacifying agents include, for example, fumed silica, polymethylmethacrylate, micronized Teflon®, boron nitride, barium sulfate, acrylate polymers, aluminum silicate, aluminum starch octenylsuccinate, calcium silicate, cellulose, chalk, corn starch, diatomaceous earth, Fuller's earth, glyceryl starch, hydrated silica, magnesium carbonate, magnesium hydroxide, magnesium oxide, magnesium trisilicate, maltodextrin, microcrystalline cellulose, rice starch, silica, titanium dioxide, zinc laurate, zinc myristate, zinc neodecanoate, zinc rosinate, zinc stearate, polyethylene, alumina, attapulgite, calcium carbonate, calcium silicate, dextran, nylon, silica silylate, silk powder, soy flour, tin oxide, titanium hydroxide, trimagnesium phosphate, walnut shell powder, or mixtures thereof. The above mentioned powders may be surface treated with lecithin, amino acids, mineral oil, silicone oil, or various other agents either alone or in combination, which coat the powder surface and render the particles hydrophobic in nature.

The opacifying agents may also comprise various organic and inorganic pigments. The organic pigments are generally various aromatic types including azo, indigoid, triphenylmethane, anthraquinone, and xanthine dyes. Inorganic pigments include iron oxides, ultramarine and chromium or chromium hydroxide colors, and mixtures thereof.

7. Suspending Agents

The compositions of the present invention may further comprise a suspending agent at concentrations effective for suspending water-insoluble material in dispersed form in the compositions or for modifying the viscosity of the composition. Such concentrations generally range from about 0.1% to about 10%, preferably from about 0.3% to about 5.0%, by weight of the composition, of suspending agent.

Suspending agents useful herein include anionic polymers and nonionic polymers. Useful herein are vinyl polymers such as cross linked acrylic acid polymers with the CTFA name Carbomer.

Other optional suspending agents include crystalline suspending agents which can be categorized as acyl derivatives, long chain amine oxides, and mixtures thereof. These suspending agents are described in U.S. Pat. No. 4,741,855. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate.

Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate.

Other long chain acyl derivatives include long chain esters of long chain fatty acids (e.g., stearyl stearate, cetyl palmitate, etc.); long chain esters of long chain alkanol amides (e.g., stearamide diethanolamide distearate, stearamide monoethanolamide stearate); and glyceryl esters (e.g., glyceryl distearate, trihydroxystearin, tribehenin) a commercial example of which is Thixin R available from Rheox, Inc. Long chain acyl derivatives, ethylene glycol esters of long chain carboxylic acids, long chain amine oxides, and alkanol amides of long chain carboxylic acids in addition to the preferred materials listed above may be used as suspending agents.

8. Paraffinic Hydrocarbons

The compositions of the present invention may contain one or more paraffinic hydrocarbons. Paraffinic hydrocarbons suitable for use in compositions of the present invention include those materials which are known for use in hair care or other personal care compositions, such as those having a vapor pressure at 1 atm of equal to or greater than about 21° C. (about 70° F.). Non-limiting examples include pentane and isopentane.

9. Propellants

The composition of the present invention also may contain one or more propellants. Propellants suitable for use in compositions of the present invention include those materials which are known for use in hair care or other personal care compositions, such as liquefied gas propellants and compressed gas propellants. Suitable propellants have a vapor pressure at 1 atm of less than about 21° C. (about 70° F.). Non-limiting examples of suitable propellants are alkanes, isoalkanes, haloalkanes, dimethyl ether, nitrogen, nitrous oxide, carbon dioxide, and mixtures thereof.

10. Other Optional Components

The compositions of the present invention may contain fragrance.

The compositions of the present invention may also contain water-soluble and water-insoluble vitamins such as vitamins B1, B2, B6, B12, C, pantothenic acid, pantothenyl ethyl ether, panthenol, biotin and their derivatives, and vitamins A, D, E, and their derivatives. The compositions of the present invention may also contain water-soluble and water-insoluble amino acids such as asparagine, alanine, indole, glutamic acid and their salts, and tyrosine, tryptamine, lysine, histadine and their salts.

The compositions of the present invention may contain a mono- or divalent salt such as sodium chloride.

The compositions of the present invention may also contain chelating agents.

The compositions of present invention may further comprise materials useful for hair loss prevention and hair growth stimulants or agents.

E. Method of Making

The compositions of the present invention, in general, may be made by mixing the ingredients together at either room temperature or at elevated temperature, e.g., about 72° C. Heat only needs to be used if solid ingredients are in the composition. The ingredients are mixed at the batch processing temperature. Additional ingredients, including electrolytes, polymers, fragrance, and particles, may be added to the product at room temperature.

F. Method of Treating Hair or Skin

The personal care compositions of the present invention are used in a conventional manner for cleansing and conditioning hair or skin. Generally, a method of treating hair or skin of the present invention comprises applying the personal care composition of the present invention to the hair or skin. More specifically, an effective amount of the personal care composition is applied to the hair or skin, which has preferably been wetted with water, and then the personal care composition is rinsed off. Such effective amounts generally range from about 1 g to about 50 g, preferably from about 1 g to about 20 g. Application to the hair typically includes working the composition through the hair such that most or all of the hair is contacted with the composition.

This method for treating the hair or skin comprises the steps of: (a) wetting the hair or skin with water; (b) applying an effective amount of the personal care composition to the hair or skin, and (c) rinsing the applied areas of skin or hair with water. These steps can be repeated as many times as desired to achieve the desired cleansing and conditioning benefit.

The personal care compositions of this invention may be used as liquids, solids, semi-solids, flakes, gels, placed in a pressurized container with a propellant added, or used in a pump spray form. The viscosity of the product may be selected to accommodate the form desired.

Non-Limiting Examples

The compositions illustrated in the following Examples illustrate specific embodiments of the compositions of the present invention, but are not intended to be limiting thereof. Other modifications can be undertaken by the skilled artisan without departing from the spirit and scope of this invention. These exemplified embodiments of the composition of the present invention provide enhanced deposition of conditioning agents to the hair and/or skin.

The compositions illustrated in the following Examples are prepared by conventional formulation and mixing methods, an example of which is described above. All exemplified amounts are listed as weight percents and exclude minor materials such as diluents, preservatives, color solutions, imagery ingredients, botanicals, and so forth, unless otherwise specified.

The following are representative of shampoo compositions of the present invention:

|  | Examples with No Silicone | | | | |
|---|---|---|---|---|---|
| Ingredient | 1 | 2 | 3 | 4 | 5 |
| Water | q.s. | q.s. | q.s. | q.s. | q.s. |
| Catonic Galactomannan [1] | 0.25 | — | 0.25 | — | — |
| Cationic Galactomannan [2] | — | 0.25 | — | 0.50 | — |
| Amphoteric Galactomannan [3] | — | — | — | — | 0.50 |
| Sodium Laureth Sulfate (SLE3S -29% active)[4] | 24.14 | 24.14 | 34.48 | 34.48 | 34.48 |
| Sodium Lauryl Sulfate (SLS - 29% active)[5] | 24.14 | 24.14 | 20.69 | 20.69 | 20.69 |
| Disodium Coco Amphodiacetate [6] | — | — | 5.0 | — | — |
| Cocoamidopropyl Betaine [7] | 6.7 | 6.7 | — | 6.7 | 13.4 |
| PPG-2 Hydroxyethyl Coco/Isostearamide[8] | 2.0 | 2.0 | 2.0 | 2.0 | 2.0 |
| Sodium Chloride [9] | 1.0 | 1.0 | 2.0 | 0.75 | 0.75 |
| Fragrance | 0.70 | 0.70 | 0.70 | 0.70 | 0.70 |
| Preservatives, pH adjusters | Up to 1% | Up to 1% | Up to 1% | Up to 1% | Up to 1% |
| Calculated: | | | | | |
| Ethoxylate Level | 2.06 | 2.06 | 2.94 | 2.94 | 2.94 |
| Sulfate Level | 3.19 | 3.19 | 3.48 | 3.48 | 3.48 |

[1] Cationic Galactomannan, MW = 200,000; CD = 2.4 meq./gram
[2] Cationic Galactomannan, MW = 200,000; CD = 3.0 meq./gram
[3] Amphoteric Galactomannan, MW = 200,000
[4] Sodium Laureth Sulfate at 29% active, supplier: P&G
[5] Sodium Lauryl Sulfate at 29% active, supplier: P&G
[6] Miranol C2M Conc NP, 40% active, supplier: Rhodia.
[7] Tegobetaine F-B, 30% active, supplier: Goldschmidt Chemicals
[8] Promidium 2, supplier Unichema
[9] Sodium Chloride USP (food grade), supplier Morton.

|  | Examples with 30 nm silicone particles | | | | | | | |
|---|---|---|---|---|---|---|---|---|
| Ingredient | 6 | 7 | 8 | 9 | 10 | 11 | 12 | 13 |
| Water | q.s. | q.s. | q.s. | q.s. | q.s. | q.s. | q.s. | q.s. |
| Cationic Galactomannan [1] | 0.25 | 0.25 | 0.25 | 0.25 | 0.25 | 0.25 | — | — |
| Cationic Galactomannan [2] | — | — | — | — | — | — | 0.25 | — |
| Amphoteric Galactomannan [3] | — | — | — | — | — | — | — | 0.25 |

-continued

| | Examples with 30 nm silicone particles | | | | | | | |
|---|---|---|---|---|---|---|---|---|
| Ingredient | 6 | 7 | 8 | 9 | 10 | 11 | 12 | 13 |
| Sodium Laureth Sulfate (SLE3S -29% active)[4] | 24.14 | 24.14 | 24.14 | 24.14 | 34.48 | 34.48 | 34.48 | 34.48 |
| Sodium Lauryl Sulfate (SLS - 29% active)[5] | 24.14 | 24.14 | 24.14 | 24.14 | 20.69 | 20.69 | 20.69 | 20.69 |
| Dimethiconol Microemulsion A [6] | 4.0 | — | — | — | 2.0 | — | 4.0 | 2.0 |
| Dimethiconol Microemulsion B [7] | — | 4.0 | — | — | — | — | — | — |
| Dimethiconol Microemulsion C [8] | — | — | 4.0 | — | — | — | — | — |
| Dimethiconol Microemulsion C [9] | — | — | — | 4.0 | — | — | — | — |
| Disodium Coco Amphodiacetate [10] | — | — | — | — | — | — | 5.0 | 5.0 |
| Cocoamdopropyl Betaine [11] | 6.7 | 6.7 | 6.7 | 6.7 | 13.4 | — | 6.7 | — |
| PPG-2 Hydroxyethyl Coco/Isostearamide[12] | 2.0 | 2.0 | 2.0 | 2.0 | — | 2.0 | — | 2.0 |
| Cocamide MEA [13] | — | — | — | — | — | — | 0.8 | — |
| Sodium Chloride [14] | 2.0 | 2.0 | 2.0 | 2.0 | 1.8 | 2.4 | 1.8 | 2.0 |
| Fragrance | 0.70 | 0.70 | 0.70 | 0.70 | 0.70 | 0.70 | 0.70 | 0.70 |
| Preservatives, pH adjusters | Up to 1% | Up to 1% | Up to 1% | Up to 1% | Up to 1% | Up to 1% | Up to 1% | Up to 1% |
| Calculated: | | | | | | | | |
| Ethoxylate Level | 2.06 | 2.06 | 2.06 | 2.06 | 2.94 | 2.94 | 2.94 | 2.94 |
| Sulfate Level | 3.19 | 3.19 | 3.19 | 3.19 | 3.48 | 3.48 | 3.48 | 3.48 |

[1] Cationic Galactomannan, MW = 200,000; CD = 2.4 meq./gram
[2] Cationic Galactomannan, MW = 200,000; CD = 3.0 meq./gram
[3] Amphoteric Galactomannan, MW = 200,000
[4] Sodium Laureth Sulfate at 29% active, supplier: P&G
[5] Sodium Lauryl Sulfate at 29% active, supplier: P&G
[6] Dow Corning Silicone Micro-emulsion DC-1870; Internal Phase Viscosity = 72,000; 30 nm particle size dimethiconol using TEA dodecyl benzene sulfonate and laureth 23 as primary surfactants, 25% active silicone
[7] Dow Corning Experimental Sample 2-1865 batch#19238-8; Internal Phase Viscosity = 44,000 cps; 30 nm particle size dimethiconol using TEA dodecyl benzene sulfonate and laureth 23 as primary surfactants, 25% active silicone
[8] Dow Corning Experimental Sample 2-1865 batcht#19238-7; Internal Phase Viscosity = 34,000 cps; 30 nm particle size dimethiconol using TEA dodecyl benzene sulfonate and laureth 23 as primary surfactants, 25% active.
[9] Experimental microemulsion Internal Phase Viscosity = 25,400 cps; 30 nm particle size dimethiconol, <1% D4 achieved through a Dow Corning Steam Stripping process, 25% active silicone, supplier: Dow Corning
[10] Miranol C2M Conc NP, 40% active, supplier: Rhodia.
[11] Tegobetaine F-B, 30% active, supplier: Goldschmidt Chemicals
[12] Promidium 2, supplier Unichema
[13] Monamid CMA, supplier Goldschmidt Chemical
[14] Sodium Chloride USP (food grade), supplier Morton.

| | Examples with 300 nm silicone particles | | | | | |
|---|---|---|---|---|---|---|
| Ingredient | 12 | 13 | 14 | 15 | 16 | 17 |
| Water | q.s. | q.s. | q.s. | q.s. | q.s. | q.s. |
| Catonic Galactomannan [1] | 0.25 | — | 0.25 | — | 0.25 | — |
| Cationic Galactomannan [2] | — | 0.25 | — | 0.25 | — | 0.25 |
| Sodium Laureth Sulfate (SLE3S -29% active)[3] | 24.14 | 24.14 | 34.48 | 34.48 | 24.14 | 24.14 |
| Sodium Lauryl Sulfate (SLS - 29% active)[4] | 24.14 | 24.14 | 20.69 | 20.69 | 24.14 | 24.14 |
| Dimethicone Emulsion [5] | 2.0 | 2.0 | 2.0 | 2.0 | 1.0 | 4.0 |
| Disodium Coco Amphodiacetate [6] | — | — | 5.0 | — | — | 5.0 |
| Cocoamdopropyl Betaine [7] | 6.7 | 6.7 | — | 6.7 | 6.7 | — |
| PPG-2 Hydroxyethyl Coco/Isostearamide[8] | 2.0 | 2.0 | 2.0 | 2.0 | 2.0 | 2.0 |
| Ethylene Glycol Distearate [9] | — | — | 1.50 | — | — | — |
| Sodium Chloride [10] | 1.3 | 1.3 | 1.3 | 1.0 | 1.3 | 1.6 |
| Fragrance | 0.70 | 0.70 | 0.70 | 0.70 | 0.70 | 0.70 |
| Preservatives, pH adjusters | Up to 1% | Up to 1% | Up to1% | Up to 1% | Up to 1% | Up to 1% |

-continued

| | Examples with 300 nm silicone particles | | | | | |
|---|---|---|---|---|---|---|
| Ingredient | 12 | 13 | 14 | 15 | 16 | 17 |
| Calculated: | | | | | | |
| Ethoxylate Level | 2.06 | 2.06 | 2.94 | 2.94 | 2.06 | 2.06 |
| Sulfate Level | 3.19 | 3.19 | 3.48 | 3.48 | 3.19 | 3.19 |

[1] Cationic Galactomannan, MW = 200,000; CD = 2.4 meq./gram
[2] Cationic Galactomannan, MW = 200,000; CD = 3.0 meq./gram
[3] Sodium Laureth Sulfate at 29% active, supplier: P&G
[4] Sodium Lauryl Sulfate at 29% active, supplier: P&G
[5] Dow Corning Dimethicone emulsion DC-1664; 3 micron particle size; 50% active
[6] Miranol C2M Conc NP, 40% active, supplier: Rhodia.
[7] Tegobetaine F-B, 30% active, supplier: Goldschmidt Chemicals
[8] Promidium 2, supplier Unichema
[9] Ethylene Glycol Distearate, EGDS Pure, supplier Goldschmidt Chemical
[10] Sodium Chloride USP (food grade), supplier Morton.

| | Examples with 30 micron avg. silicone particles | | | | | | |
|---|---|---|---|---|---|---|---|
| Ingredient | 18 | 19 | 20 | 21 | 22 | 23 | 24 |
| Water | q.s. | q.s. | q.s. | q.s. | q.s. | q.s. | q.s. |
| Catonic Galactomannan [1] | 0.25 | — | 0.25 | — | 0.25 | 0.25 | — |
| Cationic Galactomannan [2] | — | 0.25 | — | 0.25 | — | — | 0.25 |
| Sodium Laureth Sulfate (SLE3S -29% active)[3] | 24.14 | 24.14 | 48.27 | 34.48 | 41.38 | 58.62 | 13.79 |
| Sodium Lauryl Sulfate (SLS - 29% active)[4] | 24.14 | 24.14 | — | 13.79 | 6.90 | 22.41 | 3.45 |
| Sodium Alkyl Glyceryl Sulfonate (AGS-47.3% active)[5] | — | — | 6.34 | — | — | — | — |
| Dimethicone Gum [6] | 1.0 | 1.0 | 0.5 | 1.0 | 1.0 | 1.0 | 1.0 |
| Disodium Coco Amphodiacetate [7] | — | — | — | 5.0 | — | — | — |
| Cocoamdopropyl Betaine [8] | 6.7 | 6.7 | 6.7 | — | 6.7 | 6.7 | 16.67 |
| PPG-2 Hydroxyethyl Coco/Isostearamide [9] | 2.0 | 2.0 | 2.0 | 2.0 | 2.0 | 2.0 | 2.0 |
| Ethylene Glycol Distearate [10] | 1.5 | 1.5 | 1.50 | 1.5 | 1.5 | 1.5 | 1.5 |
| Sodium Chloride [11] | 1.4 | 1.2 | 1.4 | 1.7 | 1.5 | 1.4 | 1.2 |
| Fragrance | 0.70 | 0.70 | 0.70 | 0.70 | 0.70 | 0.70 | 0.70 |
| Preservatives, pH adjusters | Up to 1% | Up to 1% | Up to 1% | Up to 1% | Up to 1% | Up to 1% | Up to 1% |
| Calculated: | | | | | | | |
| Ethoxylate Level | 2.06 | 2.06 | 4.12 | 3.53 | 3.53 | 5.00 | 1.18 |
| Sulfate Level | 3.19 | 3.19 | 2.64 | 2.79 | 2.79 | 4.94 | 1.02 |
| Sulfonate Level | — | — | 0.98 | — | — | — | — |

[1] Cationic Galactomannan, MW = 200,000; CD = 2.4 meq./gram
[2] Cationic Galactomannan, MW = 200,000; CD = 3.0 meq./gram
[3] Sodium Laureth Sulfate at 29% active, supplier: P&G
[4] Sodium Lauryl Sulfate at 29% active, supplier: P&G
[5] Sodium Alkyl Glyceryl Sulfate at 47.3% active, supplier: P&G
[6] Dimethicone Gum Viscasil 330 M; 3 micron particle size; 50% active, supplier General Electric
[7] Miranol C2M Conc NP, 40% active, supplier: Rhodia.
[8] Tegobetaine F-B, 30% active, supplier: Goldschmidt Chemicals
[9] Promidium 2, supplier Unichema
[10] Ethylene Glycol Distearate, EGDS Pure, supplier Goldschmidt Chemical
[11] Sodium Chloride USP (food grade), supplier Morton.

| | Examples with Galactomannan and Cellulose | | | | | | |
|---|---|---|---|---|---|---|---|
| Ingredient | 25 | 26 | 27 | 28 | 29 | 30 | 31 |
| Water | q.s. | q.s. | q.s. | q.s. | q.s. | q.s. | q.s. |
| Catonic Galactomannan [1] | 0.25 | 0.25 | 0.25 | 0.25 | 0.50 | 0.25 | — |
| Cationic Galactomannan [2] | — | — | — | — | — | — | 0.25 |
| Polyquaternium 10 [3] | 0.10 | — | — | — | 0.10 | 0.10 | — |
| Polyquaternium 10 [4] | — | 0.10 | — | — | — | — | — |
| Polyquaternium 10 [5] | — | — | 0.10 | — | — | — | — |

-continued

| | Examples with Galactomannan and Cellulose | | | | | | |
|---|---|---|---|---|---|---|---|
| Ingredient | 25 | 26 | 27 | 28 | 29 | 30 | 31 |
| Guar Hydroxypropyl Trimonium Chloride[6] | — | — | — | 0.10 | — | — | 0.10 |
| Sodium Laureth Sulfate (SLE3S -29% active)[7] | 41.38 | 41.38 | 41.38 | 24.14 | 48.27 | 48.27 | 24.14 |
| Sodium Lauryl Sulfate (SLS - 29% active)[8] | 6.90 | 6.90 | 6.90 | 24.14 | 6.90 | 6.90 | 24.14 |
| Dimethiconol Microemulsion A [9] | 4.0 | — | — | — | 2.0 | 4.0 | 4.0 |
| Dimethiconol Microemulsion B [10] | — | 4.0 | — | — | — | — | — |
| Dimethiconol Microemulsion C [11] | — | — | 4.0 | — | — | — | — |
| Dimethiconol Microemulsion C [12] | — | — | — | 4.0 | — | — | — |
| Disodium Coco Amphodiacetate [13] | — | — | — | — | — | 5.0 | — |
| Cocoamdopropyl Betaine [14] | 6.7 | 6.7 | 6.7 | 6.7 | 6.7 | — | 6.7 |
| PPG-2 Hydroxyethyl Coco/Isostearamide[15] | 2.0 | 2.0 | 2.0 | 2.0 | 2.0 | 2.0 | 2.0 |
| Sodium Chloride [16] | 1.2 | 1.2 | 1.2 | 1.2 | 1.2 | 1.4 | 1.4 |
| Fragrance | 0.70 | 0.70 | 0.70 | 0.70 | 0.70 | 0.70 | 0.70 |
| Preservatives, pH adjusters | Up to 1% | Up to 1% | Up to 1% | Up to 1% | Up to 1% | Up to 1% | Up to 1% |
| Calculated: | | | | | | | |
| Ethoxylate level | 3.53 | 3.53 | 3.53 | 2.06 | 4.12 | 4.12 | 2.06 |
| Sulfate level | 2.79 | 2.79 | 2.79 | 3.19 | 3.17 | 3.17 | 3.19 |

[1] Cationic Galactomannan, MW = 200,000; CD = 2.4 meq./gram
[2] Cationic Galactomannan, MW = 200,000; CD = 3.0 meq./gram
[3] Polyquaterium 10 polymer with MW = 2.0 MM and charge density = 0.7
[4] UCare Polymer JR30M, MW = 2.0 MM, charge density = 1.32 meq./gram, supplier Dow Chemicals
[5] UCare Polymer KG30M, MW = 2.0 MM, charge density = 1.96 meq./gram, supplier Dow Chemicals
[6] Jaguar Excel, supplier: Rhodia.
[7] Sodium Laureth Sulfate at 29% active, supplier: P&G
[8] Sodium Lauryl Sulfate at 29% active, supplier: P&G
[9] Dow Corning Silicone Micro-emulsion DC-1870; Internal Phase Viscosity = 72,000; 30 nm particle size dimethiconol using TEA dodecyl benzene sulfonate and laureth 23 as primary surfactants, 25% active silicone
[10] Dow Corning Experimental Sample 2-1865 batch#19238-8; Internal Phase Viscosity = 44,000 cps; 30 nm particle size dimethiconol using TEA dodecyl benzene sulfonate and laureth 23 as primary surfactants, 25% active silicone
[11] Dow Corning Experimental Sample 2-1865 batch#19238-7; Internal Phase Viscosity = 34,000 cps; 30 nm particle size dimethiconol using TEA dodecyl benzene sulfonate and laureth 23 as primary surfactants, 25% active.
[12] Experimental microemulsion Internal Phase Viscosity = 25,400 cps; 30 nm particle size dimethiconol, <1% D4 achieved through a Dow Corning Steam Stripping process, 25% active silicone, supplier: Dow Corning
[13] Miranol C2M Conc NP, 40% active, supplier: Rhodia.
[14] Tegobetaine F-B, 30% active, supplier: Goldschmidt Chemicals
[15] Promidium 2, supplier Unichema
[16] Sodium Chloride USP (food grade), supplier Morton.

| | Examples with Alternate Ingredients | | | | |
|---|---|---|---|---|---|
| Ingredient | 32 | 33 | 34 | 35 | 36 |
| Water | q.s. | q.s. | q.s. | q.s. | q.s. |
| Catonic Galactomannan [1] | 0.25 | 0.50 | — | 0.50 | 0.25 |
| Sodium Laureth Sulfate (SLE3S - 29% active)[2] | 24.14 | 24.14 | 41.38 | 48.27 | 48.27 |
| Sodium Lauryl Sulfate (SLS - 29% active)[3] | 24.14 | 24.14 | 6.90 | 6.90 | 6.90 |
| Aminosilicone [4] | — | — | — | 2.0 | — |
| Aminosilicone [5] | — | — | — | — | 2.0 |
| Di-PPG-2 Myreth-10 Adipate [6] | 1.0 | — | — | — | — |
| Cocamide MEA [7] | — | — | 0.80 | — | — |
| Disodium Coco Amphodiacetate [8] | 5.0 | 5.0 | 5.0 | 5.0 | 5.0 |
| Precipitated Silica [9] | — | 1.0 | 1.0 | 1.0 | 1.0 |
| PPG-2 Hydroxyethyl Coco/Isostearamide[10] | 2.0 | 2.0 | — | 2.0 | 2.0 |
| Ethylene Glycol Distearate [11] | 1.5 | 1.5 | 1.5 | 1.5 | 1.5 |
| Sodium Chloride [12] | 1.5 | 1.5 | 1.5 | 1.5 | 1.5 |
| Fragrance | 0.70 | 0.70 | 0.70 | 0.70 | 0.70 |
| Preservatives, pH adjusters | Up to 1% | Up to 1% | Up to 1% | Up to 1% | Up to 1% |
| Calculated: | | | | | |
| Ethoxylate level | 2.06 | 2.06 | 3.53 | 4.12 | 4.12 |
| Sulfate level | 3.19 | 3.19 | 2.79 | 3.17 | 3.17 |

[1] Cationic Galactomannan, MW = 200,000; CD = 2.4 meq./gram
[2] Sodium Laureth Sulfate at 29% active, supplier: P&G
[3] Sodium Lauryl Sulfate at 29% active, supplier: P&G
[4] Aminosilicone; supplier General Electric; terminal aminopropyl substitution, viscosity ~350,000, D ~1600, M' = 2, particle size - 3 µm
[5] DC 2-8194 Aminosilicone; supplier Dow Corning, particle size ~30 nm
[6] Cromollient SCE, supplier Croda
[7] Monamid CMA, supplier Goldschmidt Chemical
[8] Miranol C2M Conc NP, 40% active, supplier: Rhodia.
[9] Tegobetaine F-B, 30% active, supplier: Goldschmidt Chemical
[10] Promidium 2, supplier Unichema
[11] Ethylene Glycol Distearate, EGDS Pure, supplier Goldschmidt Chemical
[12] Sodium Chloride USP (food grade), supplier Morton.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A personal care composition comprising:
   a) from about 0.25 wt. % to about 0.5 wt. % of a cationic cassia gum polymer derivative having a mannose to galactose ratio of 5:1 on a monomer to monomer basis, said cationic cassia gum polymer derivative is a gum hydroxypropyltrimethylammonium chloride;
      i) wherein said cationic cassia gum polymer derivative has a molecular weight of about 200,000; and
      ii) wherein said cationic cassia gum polymer derivative has a cationic charge density of about 3 meq/g;
   b) from about 14 wt. % to about 25 wt. % of an anionic surfactant system, said anionic surfactant system comprising at least one anionic surfactant and having an ethoxylate level and an anion level, wherein said anion is a sulfate,
      i) wherein said ethoxylate level is from about 2.94 to about 5, and
      ii) wherein said anion level is from about 1.5 to about 3.19;
   c) from about 0.2 wt. % to about 4 wt. % of one or more conditioning agents, wherein said conditioning agent is a silicone; and
   d) an aqueous carrier;
   wherein said personal care composition further comprises from about 0.025 wt. % to about 5 wt. % of a synthetic cationic deposition polymer having a molecular weight from about 1,000 to about 5,000,000 and a charge density from about 0.5 meq/g to about 10 meq/g;
   wherein said ethoxylate level is the percent ethoxylation multiplied by percent active ethoxylated surfactant, based upon the total weight of the composition; and
   wherein said anion level is the percent anion in ethoxylated surfactant multiplied by percent active ethoxylated surfactant, based upon the total weight of the composition, plus percent anion in non-ethoxylated surfactant multiplied by percent active non-ethoxylated surfactant, based upon the total weight of the composition.

2. A personal care composition according to claim 1, further comprising one or more surfactants selected from the group consisting of amphoteric surfactants, zwitterionic surfactants, cationic surfactants, and nonionic surfactants.

3. A personal care composition according to claim 1, further comprising from about 0.05 wt. % to about 5 wt. % of natural cationic deposition polymer having a molecular weight greater than about 5,000 and a charge density from about 0.5 meq/g to about 4.0 meq/g.

4. A personal care composition according to claim 1, further comprising one or more additional components selected from the group consisting of anti-dandruff actives, particles, opacifying agents, suspending agents, paraffinic hydrocarbons, propellants, and a mono- or divalent salt.

5. A personal care composition according to claim 1, wherein the weight ratio of said conditioning agent to said cationic cassia gum polymer derivative is at least about 2:1.

6. A personal care composition according to claim 1, wherein said conditioning agent is selected from the group consisting of silicone conditioning agents, hydrocarbon oils, polyolefins, fatty esters, and mixtures thereof.

7. A personal care composition according to claim 6, wherein said silicone conditioning agent has a particle size as measured in said personal care composition from about 1 μm to about 50 μm.

8. A personal care composition according to claim 6, wherein said silicone conditioning agent has a particle size as measured in said personal care composition from about 100 nm to about 1 μm.

9. A personal care composition according to claim 6, wherein said silicone conditioning agent has a particle size as measured in said personal care composition of less than about 100 nm.

10. A personal care composition according to claim 6, wherein said silicone conditioning agent is selected from the group consisting of organo-modified silicones and fluoro-modified silicones.

11. A personal care composition according to claim 10, wherein said organo-modified silicone comprises an organo group selected from the group consisting of alkyl groups, alkenyl groups, hydroxyl groups, amine groups, quaternary groups, carboxyl groups, fatty acid groups, ether groups, ester groups, mercapto groups, sulfate groups, sulfonate groups, phosphate groups, propylene oxide groups, and ethylene oxide groups.

12. A method of treating hair or skin, said method comprising the steps of:
   a) applying to said hair or skin a personal care composition according to claim 1; and
   b) rinsing said hair or skin with water.

* * * * *